(12) United States Patent
Andresen et al.

(10) Patent No.: US 6,979,297 B2
(45) Date of Patent: Dec. 27, 2005

(54) DIFFERENTIATING ACUTE MYOCARDIAL INFARCTION FROM OTHER ECG ABNORMALITIES

(75) Inventors: Alan V. Andresen, McMinnville, OR (US); Richard C. Myers, McMinnville, OR (US); Robert A. Warner, Tigard, OR (US); Ron H. S. Selvester, Long Beach, CA (US)

(73) Assignee: Inovise Medical, Inc., Portland, OR (US)

( * ) Notice: Subject to any disclaimer, the term of this patent is extended or adjusted under 35 U.S.C. 154(b) by 0 days.

(21) Appl. No.: 10/725,174

(22) Filed: Dec. 1, 2003

(65) Prior Publication Data

US 2004/0111037 A1 Jun. 10, 2004

Related U.S. Application Data

(60) Provisional application No. 60/430,462, filed on Dec. 2, 2002.

(51) Int. Cl.[7] .............................................. A61B 5/02
(52) U.S. Cl. .................................................... 600/500
(58) Field of Search ................................. 600/500, 507, 600/517

(56) References Cited

U.S. PATENT DOCUMENTS

| | | | | |
|---|---|---|---|---|
| 5,003,983 A | * | 4/1991 | Dingwall et al. | 600/517 |
| 5,456,261 A | * | 10/1995 | Luczyk | 600/515 |
| 5,827,195 A | * | 10/1998 | Lander | 600/509 |
| 6,038,469 A | * | 3/2000 | Karlsson et al. | 600/512 |
| 6,101,409 A | * | 8/2000 | Swanson et al. | 600/510 |
| 6,115,628 A | * | 9/2000 | Stadler et al. | 600/517 |
| 6,230,048 B1 | * | 5/2001 | Selvester et al. | 600/523 |

* cited by examiner

Primary Examiner—George Manuel
Assistant Examiner—Lenwood Faulcon, Jr.
(74) Attorney, Agent, or Firm—Jon M. Dickinson, PC; Robert D. Varitz, PC

(57) ABSTRACT

A method for differentiating acute myocardial infarction (AMI) from other ECG abnormalities. The method is performed by modeling selected ECG confounders that tend to obscure AMI evidence in the ECG waveform, and by purging a subject's ECG waveform of the effect(s) of these confounders through linking selected confounder models with an appropriate, computer-implementable purge algorithm.

4 Claims, 3 Drawing Sheets

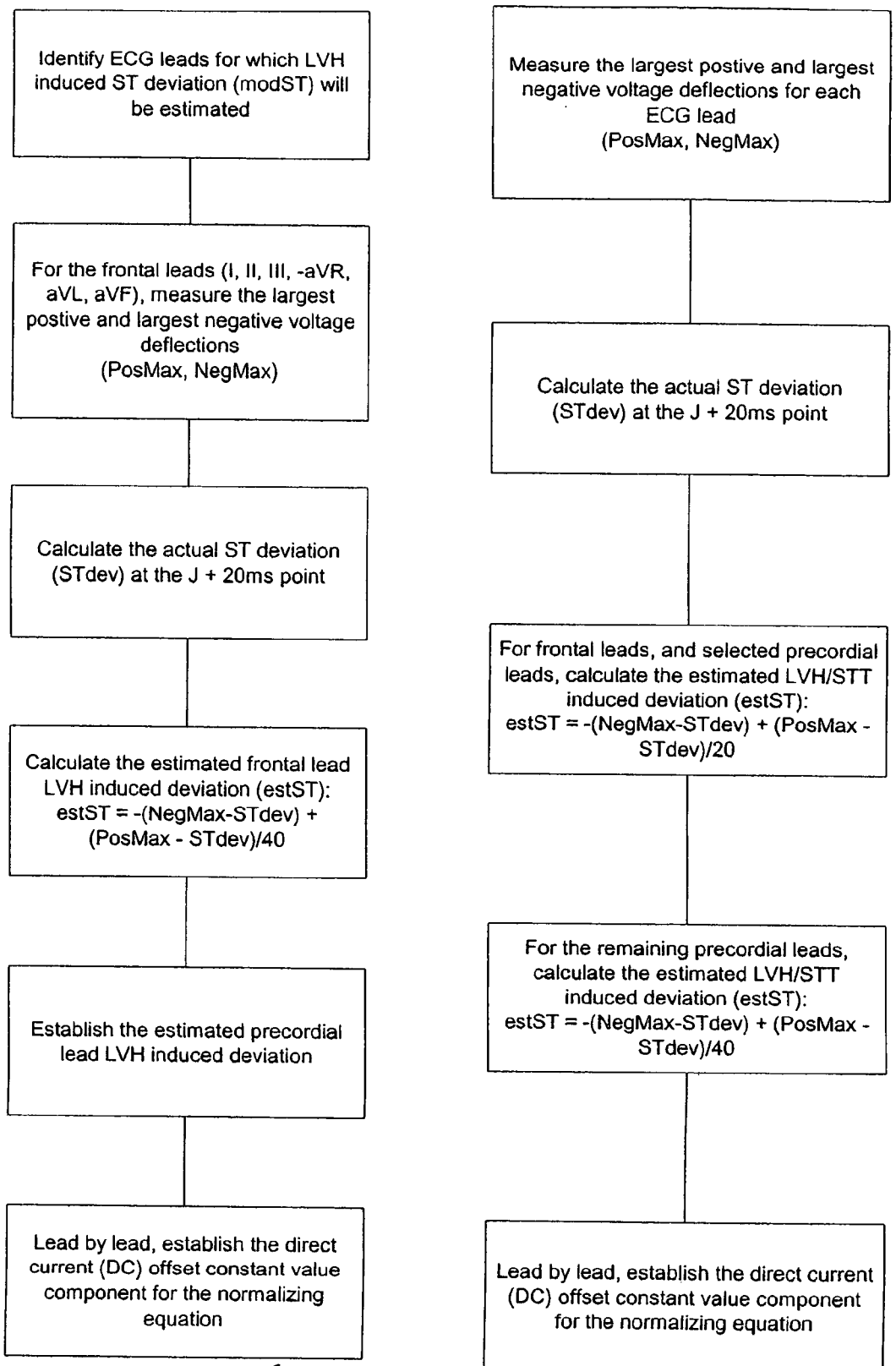

DIFFERENTIATING ACUTE MYOCARDIAL INFARCTION FROM OTHER ECG ABNORMALITIES

CROSS REFERENCE TO RELATED APPLICATION

The application claims priority to U.S. Provisional Patent Application, Ser. No. 60/430,462, filed Dec. 2, 2002, for "Differentiating Acute Myocardial Infarction From Other ECG Abnormalities". The entirety of that provisional application is hereby incorporated herein by reference.

FEDERAL SUPPORT CLAUSE

This invention was made with government support under Grant Number 2 R44 HL064485-02 awarded by the National Institutes of Health, National Heart, Lung and Blood Institute. The Government has certain rights in the invention.

BACKGROUND AND SUMMARY OF THE INVENTION

The present invention relates to improving the detection of acute myocardial infarction in the presence of certain ECG confounders, and more specifically to a method for improving such detection effectively by modeling and then removing the effect of a selected confounder on the ST segment of the PQRST ECG waveform.

Detection of acute myocardial infarction (AMI) in the presence of certain ECG confounders is challenging both for commercial electrocardiograph (ECG) algorithms, and for clinicians. The combined prevalence of Left Bundle Branch Block (LBBB), right Bundle Branch Block (RBBB), Left Ventricular Hypertrophy (LVH), and Left Ventricular Hypertrophy with STT (from the ST-T portion of the ECG waveform) Abnormality (LVH/STT) in populations of patients with documented AMI can be significant, for example, as large as about 25%. The presence of such a confounder presents a significant hurdle to the correct and accurate detection of AMI evidence in an ECG waveform, and typically does this in a variety of ways, including both the masking and mimicking of AMI's ECG "signature", principally in the ST segment of a traditional PQRST ECG waveform. This prevalence, and the obscuring effects of these confounders, highlight the need to aid clinicians in differentially diagnosing these confounding conditions from AMI.

The present invention addresses this need in a simple, practical and effective manner. Proposed according to the invention is a unique modeling and normalization procedure which focuses attention on the characteristics of the ST segment of the PQRST waveform. In particular, practice of the invention involves modeling the respective effects of the above-mentioned, several ECG confounders on this segment of the ECG waveform, thus to create, effectively, an associated reference ECG waveform that relates to each of the named, culprit confounders.

Simply and broadly stated, the method of the invention includes the steps of (a) creating a reference ECG waveform model which possesses the characteristic of an ECG waveform that is influenced by the presence of a particular selected confounder, (b) using that model, linking it relationally with an appropriate ECG purge algorithm which, in cooperation with the model, can be applied to a subject's collected ECG waveform to remove the influence of the confounder, and (c) applying that linked model and purge algorithm to such a collected ECG waveform, thus to produce a purge-processed ECG waveform that lacks the influence of the selected confounder.

These and other features involved in the implementation and practice of the present invention will now become more fully apparent as the detailed description which shortly follows is read in conjunction with the accompanying drawings.

DESCRIPTION OF THE DRAWINGS

FIG. 5 is a block/schematic diagram illustrating the logic and architecture associated with quantitative ECG modeling in relation to the presence of an ECG confounder in the category known as Left Ventricular Hypertrophy.

FIG. 6 is a block/schematic diagram illustrating the logic and architecture associated with quantitative ECG modeling in relation to the presence of an ECG confounder in the category known as Left Ventricular Hypertrophy with STT Abnormality.

DETAILED DESCRIPTION OF THE INVENTION

Figure 1:
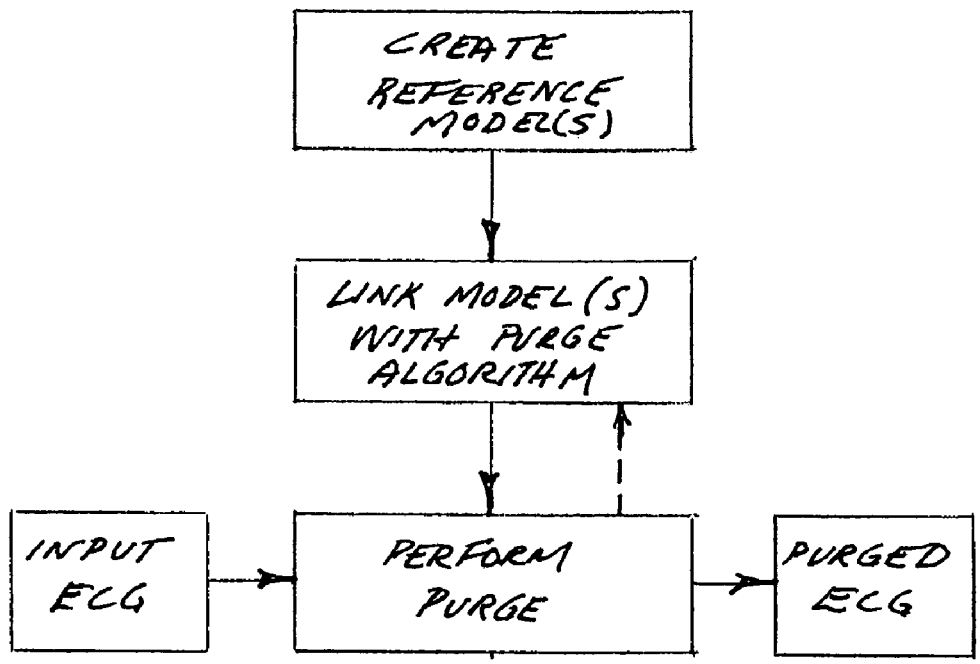
FIG. 1 is a high-level block/schematic diagram illustrating the basic method proposed by the present invention.

Turning attention now to the drawings, and referring first of all to FIG. 1, indicated generally at 10 is an organization which illustrates, from a high-level point of view, the architecture of the preferred and best mode embodiment of the methodology of the present invention. This methodology 10 in FIG. 1 is represented fundamentally by three blocks 12, 14, 16 which are labeled to indicate the principal foundation steps of the methodology of the invention. Block 12, which is labeled "Create Reference Model(s)" represents a step in the invention wherein reference ECG models are created to reflect the characteristics that make their appearance in an otherwise conventional, resting ECG waveform due to the influence of certain ECG confounders which tend to mask or mimic, and thus to obscure accurate interpretation of the ST segment of a traditional PQRST ECG waveform. These four confounders have been identified above to include LBBB, RBBB, LVH, and LVH with STT Abnormality (LVH/STT).

In the practice of the invention, these models are selectively linked in block 14 with an appropriate ECG purge algorithm, with respect to which they cooperate to enable the performance, in block 16, of a purge operation which is applied to a supplied, resting ECG waveform derived from a patient (block 18) to produce a purged ECG output waveform (block 20). This output waveform, following operation of block 16, has effectively been treated to remove the effect on the input ECG waveform of the particular ECG confounder to which the purge algorithm has been selectively model-linked.

Thus, in the practice of the invention, when a clinician, or other party, using the invention detects that there is present in a subject's resting ECG waveform the effect of any one of the four confounders just mentioned above, the user makes a selection, and effectively "signals" a system, which implements practice of the invention, to utilize, for linking with the mentioned purge algorithm, the specific pre-created model which is directed toward that detected ECG confounder. With respect to each of the four mentioned ECG confounders, taken individually, practice of the invention involves simply a single usage of the appropriate model linked with the purge algorithm to produce, and to effect, a purging operation to remove the influence of that confounder on a subject's ECG waveform. An upwardly pointing, dashed-line arrow 22 which appears in FIG. 1 directed upwardly from block 16 to block 14 represents a slightly modified practice of the invention. This modified practice is invoked when the clinician, etc., detects the combinational presence in a subject's resting ECG waveform of a particular two of the four, mentioned confounders, and namely, those which are identified as RBBB, and LVH in either of the two above-mentioned categories of LVH ECG confounders. When such a combinational situation is detected, practice of the invention involves (a) first, a use of the linked model for RBBB and the purge algorithm to treat the incoming ECG waveform in a first phase of purgation to rid the influence thereon of the RBBB confounder, and (b) thereafter, a second treatment with the purge algorithm then linked with the appropriate LVH-related confounder. Thus it is the case in this special situation where these two particular confounders are present simultaneously that a dual purgation operation is implemented.

Those skilled in the art will understand that there are various forms of conventionally implementable approaches which can be utilized to function as purge algorithms that will cause an effective "subtraction", from the incoming ECG waveform which is to be treated, of those characteristics in the waveform which cause it to be influenced by the particular confounder associated with the confounder model linked with the algorithm.

Figure 2:
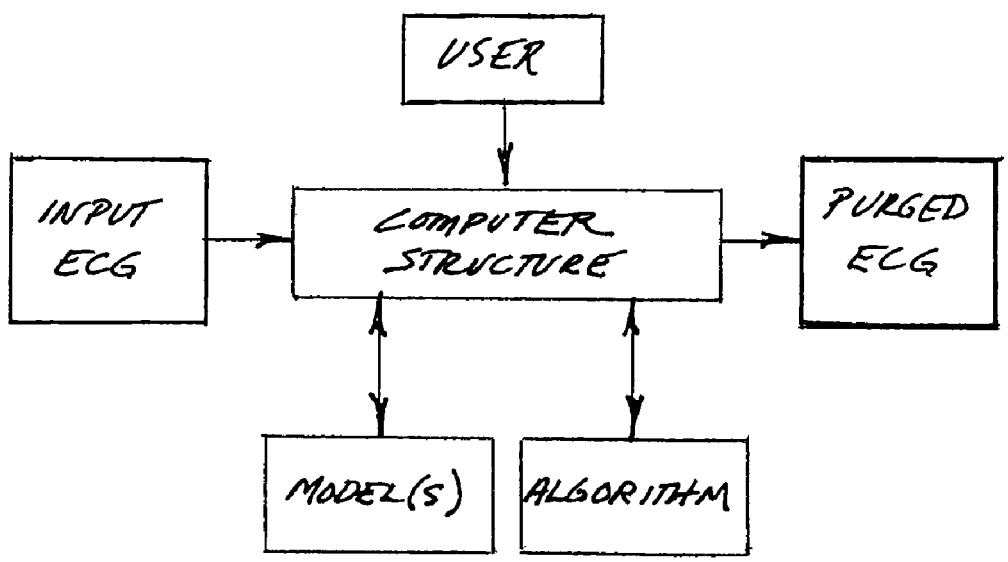
FIG. 2 is a high-level, block/schematic diagram generally illustrating a system useable to invoke and practice the methodology pictured in FIG. 1.

FIG. 2 in the drawings generally illustrates a system suitable to implement practice of invention. In this figure the user, typically a clinician, is represented by a block 24, with such a user being given appropriate control access through a suitable user interface 26 (shown as an arrow) which is operatively coupled to an appropriately programmed digital computer represented by block 28. Block 30 in FIG. 2 represents the mentioned appropriate algorithmic programming provided for computer, or computer structure, 28. Also provided to (or within) computer 28 are the particular ECG confounder models which have been created in accordance with practice of the invention, the collection of such models being represented in FIG. 2 by block 32.

Figure 3:
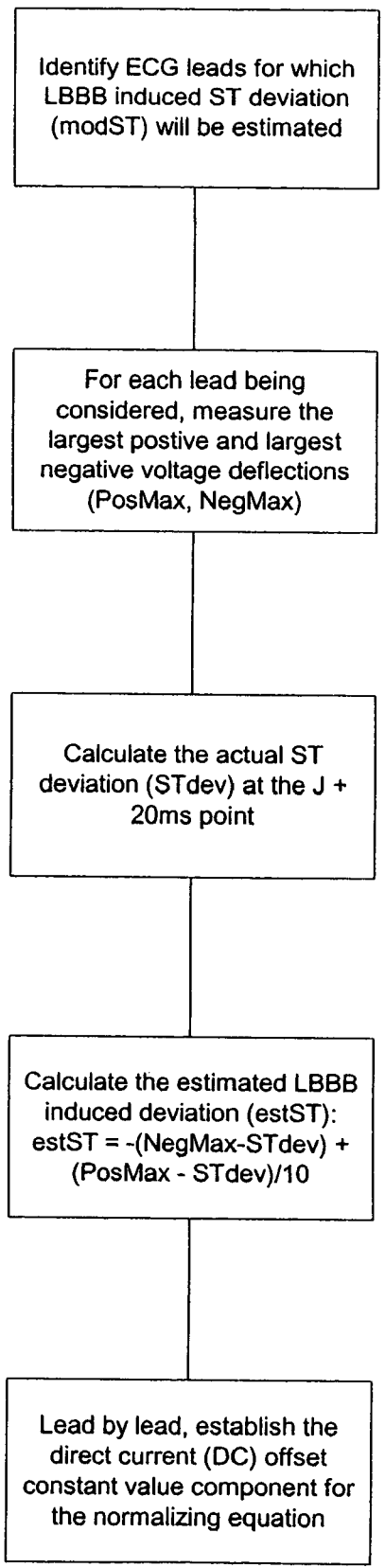
FIG. 3 is a block/schematic diagram illustrating the logic and architecture associated with quantitative ECG modeling in relation to the presence of an ECG confounder in the category known as Left Bundle Branch Block.
Figure 4:
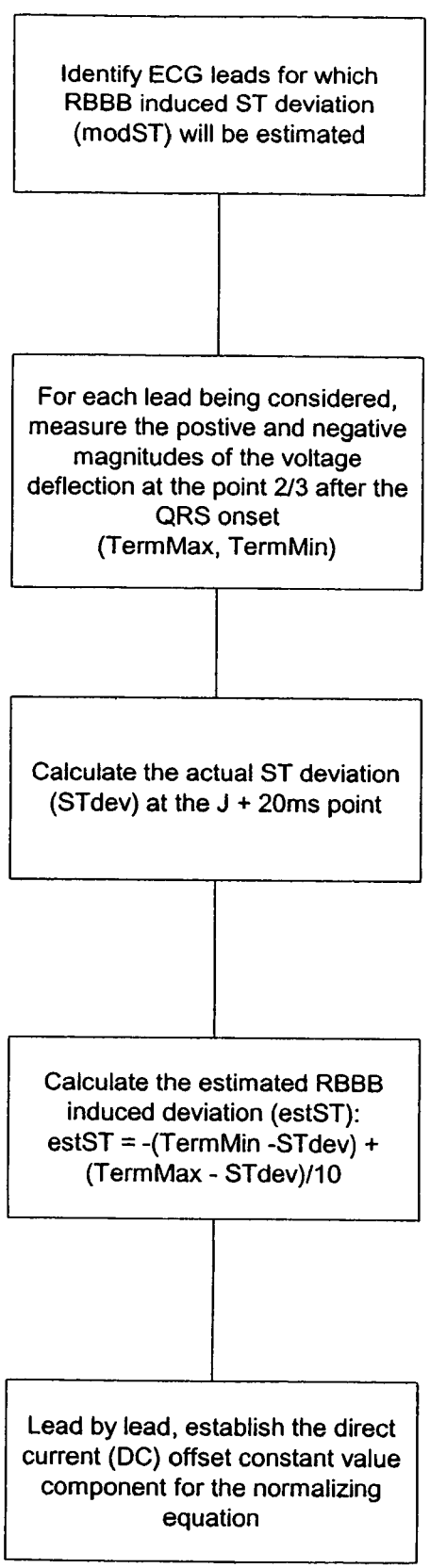
FIG. 4 is a block/schematic diagram illustrating the logic and architecture associated with quantitative ECG modeling in relation to the presence of an ECG confounder in the category known as Right Bundle Branch Block.

With this general description now given regarding the basic architecture proposed by the methodology of the present invention, and with a system which is practically useful for implementing this methodology as pictured generally in FIG. 2, we turn attention now to FIGS. 3-6, inclusive, which specifically illustrate, figure-by-figure, respective associated ECG confounder models of the four types that have been discussed so far herein. As was mentioned above in the description of the drawings, FIG. 3 describes in detail the preferred embodiment of a model, and the creation of that model, relating to the ECG confounder known as LBBB. FIG. 4 furnishes the same level and character of description of the make up and creation of a preferred model for dealing with the ECG confounder known as RBBB. Similarly, FIG. 5 describes the creation and structure of the ECG confounder model associated with LVH, and FIG. 6 provides the same level of information with respect to the ECG confounder known as LVH with STT Abnormality.

Beginning model (and creation thereof) description with FIG. 3, the LBBB model described in this figure is illustrated in the context of five operatively connected blocks 34, 36, 38, 40, 42. These blocks should be "read" from top to bottom in FIG. 3.

With reference to block 34, one begins with a quantitative estimation of LBBB induced ST deviation as a basis for normalizing the ST level measurement. The effect of ST deviation due to LBBB, utilizing knowledge possessed by those skilled in the art, is estimated lead-by-lead, and with respect to this estimation, certain ECG leads are considered to exhibit no ST deviation effect as a consequence of LBBB. These leads include –V1, –V2, –V3, –V4, and –V6.

In relation to what then takes place as described in the text presented within block 36, the magnitude of the LBBB induced ST deviation is recognized to be proportional to the magnitudes of the maximal positive and maximal negative ECG deflections in relation to the measured ST deviation level.

From these activities described with respect to blocks 34 and 36 of this LBBB confounder model and model creation, attention shifts to block 38, wherein the actual ST deviation measured from the ECG signal is used in the equation that estimates the portion of that measurement which is induced by LBBB.

The calculation set forth in block 40 which is next performed reflects the fact that the estimated LBBB induced ST deviation is 10% of the difference between the ST-to-maximum-positive-deflection and ST-to-maximum-negative-deflection differences.

Moving along to completion of what is shown in FIG. 3, and referring to block 42 therein, the final, normalized value of ST deviation is then derived from the estimated induced ST deviation plus a lead-specific empirically derived, constant value.

Turning attention now to the model, and the creation of that model, which is related to RBBB, one will observe from a comparison of FIGS. 3 and 4 that the stages involved with preparation this model are very similar to those which have just been described with regard to the building of the LBBB model. The creation and structure of this model are described with reference to five blocks 44, 46, 48, 50, 52.

More specifically, the building activity which takes place as reflected in the text presented with respect to block 44 is similar to that takes place with respect to the description given for block 34, with the exception that those certain ECG leads which are here considered to have no ST deviation effect due to RBBB include –V1, –V2, –V3, –V4, –V6, –III, and –aVL.

With respect to block 46, which has a counterpart in previously described block 36, here one recognizes that the magnitude of the RBBB induced ST deviation is proportional to the magnitudes of the maximal terminal positive and maximal terminal negative ECG deflections in relation to the measured ST deviation level.

With respect to the other three blocks that describe the architecture and building of this confounder model, the activities represented by blocks 48, 52 are essentially the same as the activities described with respect to previously discussed blocks 38, 42, respectively. The activity represented by block 50 reflects the fact that the estimated RBBB induced ST deviation is 10% of the difference between the ST-to-terminal-maximum-positive-deflection and the ST-to-terminal maximum-negative-deflection differences.

Directing attention now to FIG. 5 in the drawings which describes the model and model building relating to the confounder known as LVH, this model and its building are illustrated in six blocks 54, 56, 58, 60, 62, 64. What is represented by block 54 reflects the understanding that quantitative estimation of LVH induced ST deviation is the basis for normalizing the ST level measurement regarding LVH. Here also, the effect of ST deviation due to LVH is estimated on a lead-by-lead basis, recognizing that certain ECG leads are considered to have no ST deviation effect from LVH. These particular leads include –V1, –V2, –V3, –V4, and –V6.

In block 56 the magnitude of the LVH induced ST deviation in ECG frontal leads is recognized to be proportional to the magnitudes of the maximal positive and maximal negative ECG deflections in relation to the measured ST deviation level.

In block 58 one recognizes that the actual ST deviation measured from, the ECG signal is to be used in the equation that estimates the portion of that measurement which is induced by LVH.

Block 60 reflects the performance of a calculation based upon the understanding that the estimated LVH induced ST deviation in the frontal leads is 2.5% of the difference between the ST-to-maximum-position-deflection and the ST-to-maximum-negative-position-deflection differences.

Block 62 reflects the fact that the estimated LVH induced ST deviation in the precordial leads is a lead-specific, empirically derived constant value.

With attention now turned to block 64, the final, normalized value of ST deviation is derived from the estimated induced ST deviation plus a lead-specific empirically derived, constant value.

The model which is related to LVH with STT Abnormality is described, as mentioned earlier, in FIG. 6 which provides this description through five blocks 66, 68, 70, 72, 74 which appear in that figure.

Turning attention first to block 66, here one recognizes that the quantitative estimation of LVH/STT induced ST deviation is the basis for normalizing the ST level measurement. The effect of ST deviation due to LVH/STT is estimated lead-by-lead. Here also, the magnitude of the LVH/STT induced ST deviation in the ECG frontal leads is recognized to be proportional to the magnitudes of the maximal positive and maximal negative ECG deflections in relation to the measured ST deviation level.

Block 68 reflects the fact that the actual ST deviation measured from the ECG signal is to be used in the equation that estimates the portion of that measurement which is induced by LVH/STT.

Block 70 describes, now, a calculation recognizing that estimated LVH/STT induced deviation in the frontal leads and precordial leads V1, V2, V3, –V1, –V2, –V3 is 5% of the difference between the ST-to-maximum-positive-deflection and the ST-to-maximum-negative-deflection differences.

Block 72 describes a performed calculation which recognizes that estimated LVH/STT induced deviation for the remaining precordial leads is 2.5% of the difference between the ST-to-maximum-position-deflection and the ST-to-maximum-negative-deflection differences.

Addressing attention finally to block 74, this block reflects the fact that the final, normalized value of ST deviation is derived from the estimated induced ST deviation plus a lead-specific empirically derived, constant value.

With regard to the representations now of these four ECG confounder models, the descriptions thereof, and the creations thereof, as fully described above with respect to FIGS. 3–6, inclusive, those skilled in the art will recognize both the natures and the ways of constructing these models so as to implement them in the practice of the present invention.

With these models constructed, and utilized in a system such as that pictured in FIG. 2 to practice a methodology such as that presented clearly in FIG. 1, one will see that a unique and effective methodology is provided for removing from the ST segment of the PQRST ECG waveform those effects therein produced by these confounders, which effects tend to obscure "access" to AMI information otherwise effectively hidden by the presence of these confounders. As a consequence, the methodology of the invention makes possible the review of a subject's ECG waveform in a manner which provides a much clearer view about whether or not evidence of AMI is present in the subject's ECG waveform. In the special case where one detects the co-presence of the two confounders mentioned earlier that may sometime coexist, namely, RBBB and either one of the two mentioned LVH-based confounders, the methodology of the invention proposes a dual pass through the purge-algorithm implementation of the invention, utilizing first the RBBB confounder model to remove effectively the influence of the RBBB confounder, and thereafter a purge activity based upon the appropriate LVH-based confounder model to remove the effect of that confounder.

Accordingly, while a preferred manner of practicing the invention, described in its best mode form, has been illustrated and described herein, it is appreciated that certain variations and modifications may come to the minds of those skilled in the art based upon their understandings of this invention, and we recognize that all such variations and modifications come within the scope of the present invention.

We claim:

1. A method for clarifying a subject's collected ECG waveform for analysis by first effectively removing a recognized, embedded influence over certain characteristics of that waveform which exists by virtue of the physiologic presence, in the subject's heart, of a particular ECG confounder, said method comprising creating a reference ECG waveform model which possesses the characteristics of an ECG waveform that is influenced by the presence of the particular confounder, linking the model to an ECG purge algorithm which, in cooperation with the model, can be applied to such a subject's collected ECG waveform to remove the influence of the confounder, and applying the linked model and purge algorithm to such a collected ECG waveform, thus to produce a purge-processed ECG waveform that lacks the influence of the selected confounder, wherein said creating comprises quantitative modeling of ST abnormalities due to the presence of Left Bundle Branch Block (LBBB) within the traditional 12-lead resting ECG, and said modeling includes (a) identifying ECG leads for which LBBB induced ST deviation (modST) will be estimated, (b) for each such lead being considered, measuring the largest positive and the largest negative voltage deflections (PosMax, NegMax), (c) calculating the actual ST deviation (STdev) at the J+20 ms point, (d) calculating the estimated LBBB induced deviation: (estST): estST=–(NegMax-STdev) +(PosMas–STdev)/10, and (e) establishing, lead-bylead, the direct current (DC) offset constant value component for use in a normalizing equation.

2. A method for clarifying a subject's collected ECG waveform for analysis by first effectively removing a recognized, embedded influence over certain characteristics of that waveform which exists by virtue of the physiologic presence, in the subject's heart, of a particular ECG confounder, said method comprising creating a reference ECG waveform model which possesses the characteristics of an ECG waveform that is influenced by the presence of the particular confounder, linking the model to an ECG purge algorithm which, in cooperation with the model, can be applied to such a subject's collected ECG waveform to remove the influence of the confounder, and applying the linked model and purge algorithm to such a collected ECG waveform, thus to produce a purge-processed ECG waveform that lacks the influence of the selected confounder, wherein said creating comprises to quantitative modeling of ST abnormalities due to the presence of Right Bundle Branch Block (RBBB) within the traditional 12-lead resting ECG, and said modeling includes (a) identifying ECG leads for which RBBB induced ST deviation (modST) will be estimated, (b) for each such lead being considered, measuring the positive and negative magnitudes of the voltage deflection at the point ⅔ after the QRS onset (TermMax, TermMin), (c) calculating the actual ST deviation (STdev) at the J+20 ms point, (d) calculating the estimated RBBB induced deviation (estST): estST=−(TermMin−STdev)+(TermMax−STdev)/10, and (e) establishing, lead-by-lead, the direct current (DC) offset constant value component for use in a normalizing equation.

3. A method for clarifying a subject's collected ECG waveform for analysis by first effectively removing a recognized, embedded influence over certain characteristics of that waveform which exists by virtue of the physiologic presence, in the subject's heart, of a particular ECG confounder, said method comprising creating a reference ECG waveform model which possesses the characteristics of an ECG waveform that is influenced by the presence of the particular confounder, linking the model to an ECG purge algorithm which, in cooperation with the model, can be applied to such a subject's collected ECG waveform to remove the influence of the confounder, and applying the linked model and purge algorithm to such a collected ECG waveform, thus to produce a purge-processed ECG waveform that lacks the influence of the selected confounder, wherein said creating comprises quantitative modeling of ST abnormalities due to the presence of Left Ventricular Hypertrophy within the traditional 12-lead resting ECG, and said modeling includes (a) identifying ECG leads for which LVH induced ST deviation (modST) will be estimated, (b) for the frontal leads (I, III, III, −aVR, aVL, aVF), measuring the largest positive and largest negative voltage deflections (PosMax, NegMax), (c) calculating the actual ST deviation (STdev) at the J+20 ms point, (d) calculating the estimated frontal lead LVH induced deviation (estST): estST=−(NegMax−STdev)+(PosMax−STdev)/40, (e) establishing the estimated precordial lead LVH induced deviation, and (f) establishing, lead-by-lead, the direct current (DC) offset constant value component for use in a normalizing equation.

4. A method for clarifying a subject's collected ECG waveform for analysis by first effectively removing a recognized, embedded influence over certain characteristics of that waveform which exists by virtue of the physiologic presence, in the subject's heart, of a particular ECG confounder, said method comprising creating a reference ECG waveform model which possesses the characteristics of an ECG waveform that is influenced by the presence of the particular confounder, linking the model to an ECG purge algorithm which, in cooperation with the model, can be applied to such a subject's collected ECG waveform to remove the influence of the confounder, and applying the linked model and purge algorithm to such a collected ECG waveform, thus to produce a purge-processed ECG waveform that lacks the influence of the selected confounder, wherein said creating comprises quantitative modeling of ST abnormalities due to the presence of Left Ventricular Hypertrophy with STT abnormalities within a traditional 12-lead resting ECG, and said modeling includes (a) for each such lead being considered, measuring the largest positive and largest negative voltage deflections (PosMax, NegMax), (b) calculating the actual ST deviation (STdev) at the J+20 ms point, (c) for frontal leads, and for selected precordial leads calculating the estimated LVH/STT induced deviation (estST): estST=−(NegMax−STdev)+(PosMax−STdev)/20, (d) for the remaining precodial leads, calculating the estimated LVH/STT induced deviation (estST): estST=−(NegMax−STdev)+(PosMax−STdev)/40, and (e) establishing, lead-by-lead, the direct current (DC) offset constant value component for use in a normalizing equation.

* * * * *